US008010206B2

(12) United States Patent
Dai et al.

(10) Patent No.: US 8,010,206 B2
(45) Date of Patent: Aug. 30, 2011

(54) EXTERNAL COIL ASSEMBLY FOR IMPLANTABLE MEDICAL PROSTHESES

(75) Inventors: Rongqing Dai, Valencia, CA (US); Dao Min Zhou, Saugus, CA (US); Robert J. Greenberg, Los Angeles, CA (US); John Gord, Venice, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 395 days.

(21) Appl. No.: 11/924,423

(22) Filed: Oct. 25, 2007

(65) Prior Publication Data
US 2008/0082147 A1 Apr. 3, 2008

Related U.S. Application Data

(62) Division of application No. 11/529,809, filed on Sep. 29, 2006.

(51) Int. Cl.
*A61N 1/378* (2006.01)
(52) U.S. Cl. ....... 607/60; 607/61; 343/742; 340/539.12; 340/539.16; 307/104
(58) Field of Classification Search ............. 607/60–61; 343/742; 340/539.12, 539.16; 307/104
See application file for complete search history.

(56) References Cited

U.S. PATENT DOCUMENTS

| | | |
|---|---|---|
| 4,494,545 A | 1/1985 | Slocum |
| 4,542,532 A | 9/1985 | McQuilkin |
| 4,573,481 A | 3/1986 | Bullara |
| 4,628,933 A | 12/1986 | Michelson |
| 4,837,049 A | 6/1989 | Byers |
| 5,109,844 A | 5/1992 | de Juan, Jr. et al. |
| 5,215,088 A | 6/1993 | Normann et al. |
| 5,935,155 A | 8/1999 | Humayun et al. |
| 6,137,447 A * | 10/2000 | Saitoh et al. ................ 343/742 |
| 6,298,271 B1 | 10/2001 | Weijand |
| 6,348,070 B1 | 2/2002 | Teissl |
| 6,400,989 B1 | 6/2002 | Eckmiller |
| 6,458,157 B1 | 10/2002 | Suaning |
| 6,591,139 B2 | 7/2003 | Loftin |
| 2002/0188282 A1 | 12/2002 | Greenberg |
| 2004/0155290 A1 | 8/2004 | Mech et al. |
| 2005/0222624 A1 | 10/2005 | Greenberg et al. |
| 2005/0288733 A1 | 12/2005 | Greenberg et al. |
| 2005/0288734 A1 | 12/2005 | Greenberg et al. |
| 2006/0036295 A1 | 2/2006 | Greenberg et al. |
| 2006/0167528 A1 | 7/2006 | Roy et al. |
| 2008/0027513 A1 * | 1/2008 | Carbunaru ................ 607/60 |

FOREIGN PATENT DOCUMENTS

| | | |
|---|---|---|
| EP | 0 154 563 A2 | 9/1985 |
| EP | 1 481 708 A1 | 12/2004 |
| WO | WO 01/05467 A1 | 1/2001 |

OTHER PUBLICATIONS

Eugene De Juan, et al.; Retinal Tacks; American Journal of Opthalmology 99; pp. 272-274, Mar. 1985.

* cited by examiner

*Primary Examiner* — Niketa Patel
*Assistant Examiner* — Rex R Holmes
(74) *Attorney, Agent, or Firm* — Scott B. Dunbar; Alessandro Steinfl

(57) ABSTRACT

Methods and devices for inductively coupled implants on the human or animal body are disclosed. An external coil assembly to be used with the implant has a transmitting coil and one or more receiving coils. The number of the receiving coils, their distance from the transmitting coil and their shape is chosen to reduce the influence of a noise signal received by the external coil assembly.

4 Claims, 7 Drawing Sheets

EXTERNAL COIL ASSEMBLY FOR IMPLANTABLE MEDICAL PROSTHESES

CROSS REFERENCE TO RELATED APPLICATIONS

This application is a divisional of application Ser. No. 11/529,809, entitled "External Coil Assembly for Implantable Medical Prostheses", filed Sep. 29, 2006. The present invention is related to U.S. Pub. App. No. 2005/0222624 (Retinal Prosthesis with Side Mounted Inductive Coil) and U.S. Pub. App. No. 2005/0288734 (Visuai Prosthesis with Operational Data Telemetry), the disclosures of both of which are incorporated herein by reference in their entirety.

FEDERALLY SPONSORED RESEARCH

This invention was made with government Support under grant no. R24EY12893-01, awarded by the National Institutes of Health. The U.S. Government has certain rights in the invention.

BACKGROUND

1. Field

The present disclosure relates to devices implantable on the animal or human body. In particular, it relates to an external coil assembly for implantable medical prostheses.

2. Related Art

In inductively powered retinal prostheses, coils are used to transmit and receive RF power in both external and implant ends. Reference can be made, for example, to U.S. Pat. No. 5,935,155 (Visual Prosthesis and Method of Using Same), incorporated herein by reference in its entirety. Due to the low power nature of the implant device and the limited implant coil size, it imposes difficulties to retrieve the low level feedback signals at the external side in the presence of a strong magnetic field created by the external transmitting power carrier. This is especially true when the back telemetry signal frequency is not much far away from the power carrier. In the case of retinal prosthesis when the implant coil is mechanically linked to the eyeball, the eyeball movement compromises the coupling condition between the external and implant coils and therefore makes the back telemetry signal condition at the external receiving end worse. There is a need for an apparatus and method to reduce and possibly minimize the power carrier component in the received spectrum and therefore to improve the back telemetry reliability.

In 1755 LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising a prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparati to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across retinal neuronal cell membranes, which can initiate retinal neuronal action potentials, which are the means of information transfer in the nervous system.

Based on this mechanism, it is possible to input information into the nervous system by coding the sensory information as a sequence of electrical pulses which are relayed to the nervous system via the prosthetic device. In this way, it is possible to provide artificial sensations including vision.

Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the retinal neurons, and avoid undue compression of the retinal neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated a cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sciera, effectively pinning the retina against the choroid and the posterior aspects of the globe. Retinal tacks are one way to attach a retinal electrode array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY

According to a first aspect of the present disclosure, an external coil assembly for an inductively coupled implant on the human or animal body is disclosed, comprising: a transmitting coil, adapted to transmit signals to the implant; a first receiving coil, adapted to receive signals from the implant, the first receiving coil exhibiting a first coupling coefficient with the transmitting coil; and a second receiving coil, the second receiving coil exhibiting a second coupling coefficient with the transmitting coil, wherein the first coupling coefficient is substantially identical to the second coupling coefficient.

According to a second aspect of the present disclosure, an inductive assembly adapted to communicate with an implant on the human or animal body is disclosed, comprising: a transmitting inductor; a first receiving inductor, comprising a first coil, a first substrate associated with the first coil, and a first metal shield connected with the first substrate; and a second receiving inductor, comprising a second coil, a second substrate associated with the second coil, and a second metal shield connected with the second substrate, wherein the first receiving inductor and the second receiving inductor are located on different sides of the transmitting inductor and substantially equidistant from the transmitting inductor.

According to a third aspect of the present disclosure, an inductive transceiver is disclosed, comprising: a transmitting coil; and a receiving coil, wherein a coupling coefficient between the transmitting coil and the receiving coil is substantially equal to zero, and wherein the inductive transceiver is adapted to interact with an implant implanted in a human or animal body and is adapted to be located externally to the human or animal body.

According to a fourth aspect of the present disclosure, an inductive assembly adapted to be coupled with an implant on a human or animal body and to be located externally to the implant is disclosed, the assembly comprising: a first inductor, the first inductor defining a first area inside the first inductor and a second area outside the first inductor; a second inductor located proximate to the first inductor, the second inductor having a symmetrical shape comprised of a first second inductor region and a second second inductor region the first second inductor region defining a third area inside the first second inductor region, the second second inductor region defining a fourth area inside the second second inductor region, wherein intersection between the first area and the third area defines a first magnetic flux region, intersection between the first area and the fourth area defines a second magnetic flux region, intersection between the second area and the third area defines a third magnetic flux region, intersection between the second area and the fourth area defines a fourth magnetic flux region, and wherein magnetic flux intensity through the first magnetic flux region and the second magnetic flux region is substantially equal and opposite to magnetic flux intensity through the second magnetic flux region and the third magnetic flux region.

According to a fifth aspect of the present disclosure, a method to improve receiving sensitivity in an external coil assembly for an inductively coupled implant on the human or animal body is disclosed, wherein the external coil assembly comprises a transmitting coil and a receiving coil, the implant comprises an implant coil, the transmitting coil allows transmission of a forward telemetry signal at a carrier frequency to the implant, and the implant is adapted to send a back telemetry signal to the external coil assembly, the method comprising: adjusting position of the receiving coil with respect to the transmitting coil to reduce influence of a noise signal at the carrier frequency received by the external coil assembly in addition to the back telemetry signal.

According to a sixth aspect of the present disclosure, a visual prosthesis is disclosed, comprising: an image capture device converting a visual image to a data stream; a video processing unit receiving the data stream, applying filters to the data stream and providing a processed data stream; a transmitting coil, transmitting the processed data stream; an implanted secondary coil receiving the processed data stream and transmitting operational data telemetry; implanted electronics receiving the processed data stream from the implanted secondary coil stimulating visual neural tissue and producing the operational data telemetry; a first receiving coil, adapted to receive signals from the implanted secondary coil, the first receiving coil exhibiting a first coupling coefficient with the transmitting coil; and a second receiving coil, the second receiving coil exhibiting a second coupling coefficient with the transmitting coil, wherein the first coupling coefficient is substantially identical to the second coupling coefficient.

In accordance with the present disclosure, the back telemetry signals sent by the implant are reliably retrieved in the presence of a strong magnetic field imposed by the PF carrier of the power transmitter, without increasing the complexity of the receiver circuits and compromising the cosmetics of mechanical configuration of the external coils.

DETAILED DESCRIPTION

Figures 1, 2:
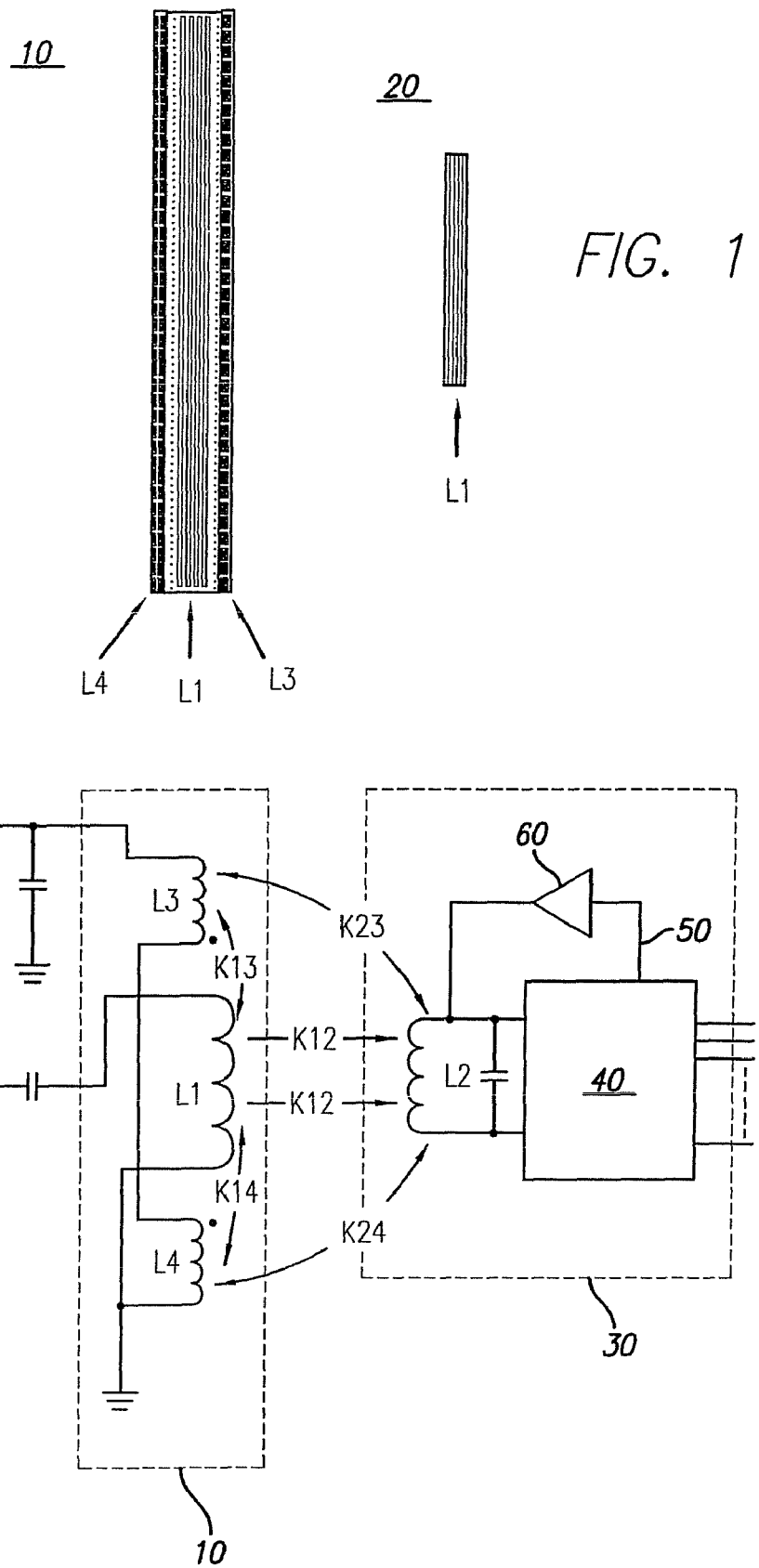
FIG. 1 shows a first embodiment of an external coil assembly in accordance with the present disclosure.
FIG. 2 shows an electrical diagram of the embodiment of FIG. 1.

FIG. 1 shows a first embodiment of an external coil assembly 10 inductively coupled with an implant coil 20. The external coil assembly 10 comprises inductors L1, L3 and L4. The implant coil 20 comprises inductor L2. Throughout the present specification, the various inductors will be described as coils, for exemplary purposes.

With reference to the external coil assembly 10, coil L1 represents a transmitting coil, and coils L3, L4 represent receiving coils. Transmitting coil L1 allows a forward telemetry (FT) signal to be sent to implant coil 20 or L2. Receiving coils L3 and L4 allow a back telemetry (BT) signal to be received from the implant coil 20 or L2. The concept of FT signals and BT signals is known to the person skilled in the art. See, for example, U.S. Pub. App. No. 2005/0288734 (Visual Prosthesis with Operational Data Telemetry), incorporated herein by reference in its entirety. In accordance with this embodiment, transmitting coil L1 is located between receiving coils L3 and L4. Transmitting coil L1 is separated from receiving coils L3, L4 by means of a dielectric, e.g. air. A possible distance between coil L1 and coil L4 or coil L1 and coil L3 is about 2 mm. In the embodiment of FIG. 1, coil L3 is identical to coil L4. Both coils L3 and L4 are placed at a same distance from L1. However, embodiments where L3 is different from L4 can also be envisaged.

FIG. 2 shows an electrical diagram of the first embodiment of FIG. 1. An FT input signal amplified through power amplifier PA is fed to transmitting coil L1 and inductively received by implant coil L2. Implant coil L2 is part of an implant 30, further comprising a transceiver or stimulator 40. Implant 30 will not be described herewith in detail. A possible example of implant 30 can be found in U.S. Pub. App. No. 2005/0222624 (Retinal Prosthesis with Side Mounted Inductive Coil), incorporated herein by reference in its entirety. incorporated herein by reference in its entirety. Among other functions, transceiver 40 sends a back telemetry (BT) signal to coil L2 through driver 60. The BT signal sent through coil L2 is inductively received by receiver coils L3 and L4 and sent to a receiver circuit 70.

Magnetic coupling coefficients between the various pairs of coils are formed. The coupling coefficient measures the mutual inductance between two inductors. The coupling coefficient between coils L1 and L2 is defined as $$K_{12} = \frac{M_{12}}{\sqrt{L_1 L_2}},$$

where M12 is the mutual inductance between coils L1 and L2. For two spiral type coils, the value of their coupling coefficient is determined by their separation distance, coil dimensions, and their alignment. In particular, the coupling coefficient increases as the two coils move closer, and decreases as they move farther.

On the external coil assembly side, coupling coefficient K13 defines the magnetic coupling between L1 and L3. Similarly, coupling coefficient K14 defines the coupling between L1 and L4. When the external coil assembly 10 interacts with the implant coil 20, further coupling coefficients K12, K23 and K24 are defined, the meaning of which is identical to the one discussed above.

In accordance with the present disclosure K13 is made to be substantially the same as K14, i.e. K13≈K14. In the present embodiment, coils L3 and L4 are arranged in a differential configuration in the circuit. In particular, with reference to FIG. 2, the lower portion of L3 is in-phase with the upper portion of L4, as shown by the position of the dots. Therefore, if the coils L3 and L4 are arranged so that they receive equal electromagnetic field strength from the L1), the net field strength L3 and L4 receive from L1 is zero, thus obtaining the desired condition of rejecting the interferences from L1. In practical realization, the exact fulfillment of the K13=K14 requirement may not be achievable and what is relevant is that K13 is substantially equal to K14, i.e. K13≈K14. With "substantially equal" a condition is intended where the direct influence of L1 on L3 and L4 when the BT signal is received from L2 is substantially reduced.

On the other hand, the coupling relation of the BT coils to the implant coil L2 is different as to L1. By positioning L3 closer to L2 than L4, as shown in FIG. 1, K23 is made greater than K24, i.e. K23>K24. As a result, the front coil L3 will receive a stronger field strength from implant coil L2 than the back coil L4. The net output produced by the BT coils L3 and L4 from the implant coil is the difference between the signals received by L3 and L4 individually.

The signals transmitted back from the implant 30 will include the BT signals and reflected carrier signals. However, the reflected carrier signals coupled from L2 are much weaker in strength than the direct transmitting carrier signals coupled from L1. Therefore, by rejecting the direct transmitting carrier signals from L1, the arrangement shown in FIGS. 1 and 2 provides the BT signals with a better signal-to-carrier noise ratio than using a single back telemetry receiving coil. The receiver circuit 70 will then condition and decode the BT signal.

Figure 3:
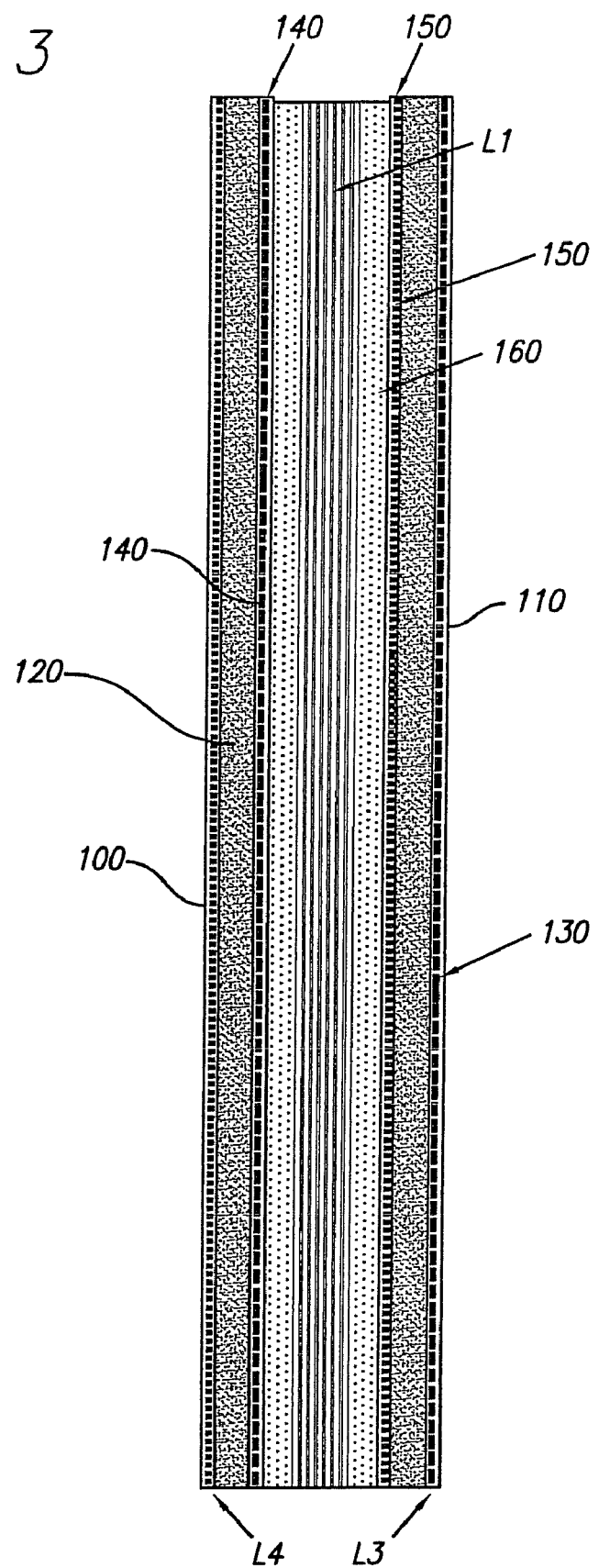
FIG. 3 shows a second embodiment of the present disclosure.

FIG. 3 shows a further embodiment of the present disclosure, wherein each one of inductors L3, L4 can comprise: a coil layer 100 (or 110), an insulator (or substrate) layer 120 (or 130), and an electrical shield layer 140 (or 150). This embodiment can be readily realized with a double-layered printed circuit board (PCB) in which the coil and shield are made of copper traces and the insulation is the PCB substrate. As usual, L4 and L3 are separated from L1 by way of an insulator 160, e.g. air. The presence of the metallic shield layer shunts the stray capacitors around transmitting coil L1 so that the tuning condition is not affected by the variation of the coil placement relative to the body. It also prevents the displacement current produced by the transmitting coil L1 from flowing through the human body. Incidentally, also the implant coil L2 can be shielded for the same purpose.

In order to reduce the loss of the transmitting power from L1 caused by Eddy currents and thermal effect, thin traces or wires with good conductivity such as copper can be used for the receiving coils L3 and L4 and also the electrical shielding. In practical applications, the physical specifications of the coils, such as the coil dimensions, separations between the coils in the assembly, and coil configurations (turns, pitches, wire diameters etc.) can be optimized for the requirements of power and range of movement between coil L1 and the implant coil L2.

Figure 4:
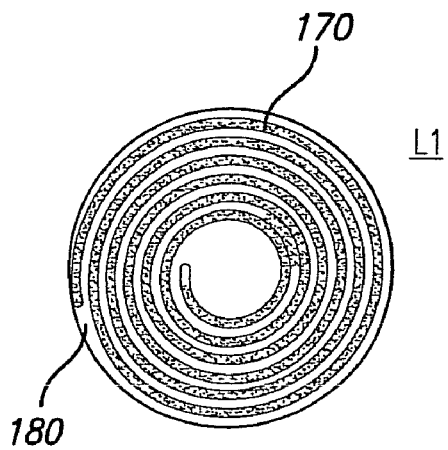
FIGS. 4 and 5A-5C show sectional views referring to the second embodiment.

FIG. 4 shows a top sectional view of an exemplary configuration of transmitting inductor L1, comprising a coil 170 and insulator 180 between the windings of the coil. Coil 170 can either be comprised of single layer or multi-layer turns of conductors, such as copper. For applications demanding high power, multi-stranded Litz wires can be used for the conductors in coil 170 in order to reduce power loss due to skin effect.

Figure 5A:
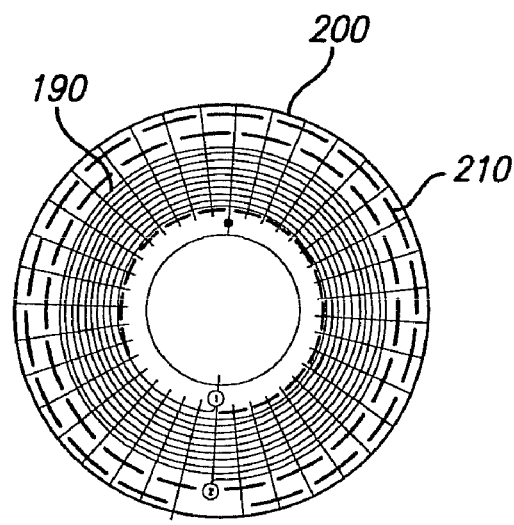
Figure 5B:
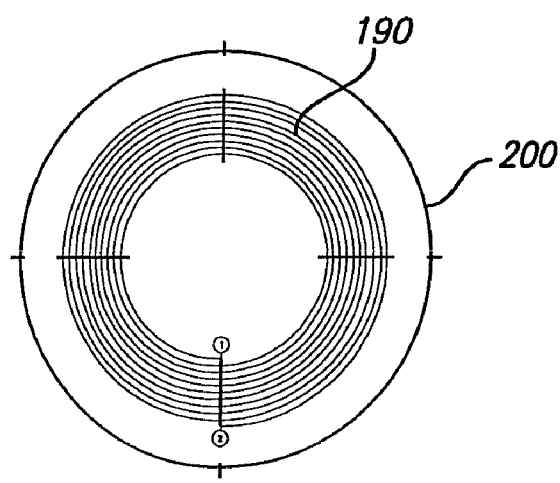
Figure 5C:
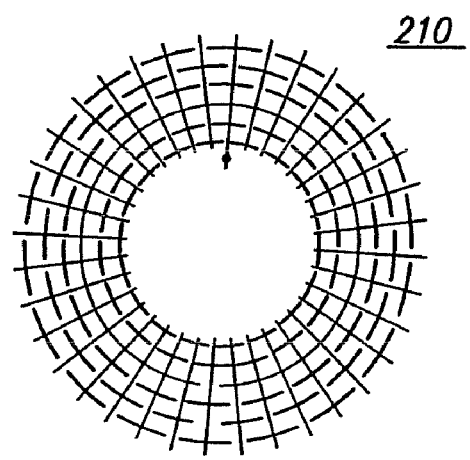

FIG. 5A shows a top sectional view of an exemplary configuration of inductor L3 or L4, comprising a coil 190, a substrate 200, and a metallic shield 210 (shown in dotted lines). FIG. 5B shows a partial view of the coil 190 and the substrate 200. FIG. 5C shows a partial view of the metallic shield 210. The conductors (or traces) in 210 are arranged in such a way that they do not form any closed circles (circuits).

The electrical shielding can be connected to a low impedance point and stable electrical potential of the external assembly (e.g. the RF power ground) so that the stray capacitances are stabilized and the coupling or displacement path between the coil and the body is shunted. In order to minimize the shielding effects to the magnetic field by the metal materials, low resistivity materials can be used, so that any Eddy current formed in the metal consumes a small amount of power. A mesh type structure with thin wires can also be used, without forming any closed circuit in the shield layer that acts like a coil to loop electrical currents. This shield pattern is schematically indicated by reference numeral 210 in FIGS. 5A and 5C. The spaces between the traces shown in FIG. 5C can be tuned close to the gap distance between the L1 coil surface and the shield layer for a balance between good shielding performance and low degradation to the magnetic field.

Figures 6A, 6B:
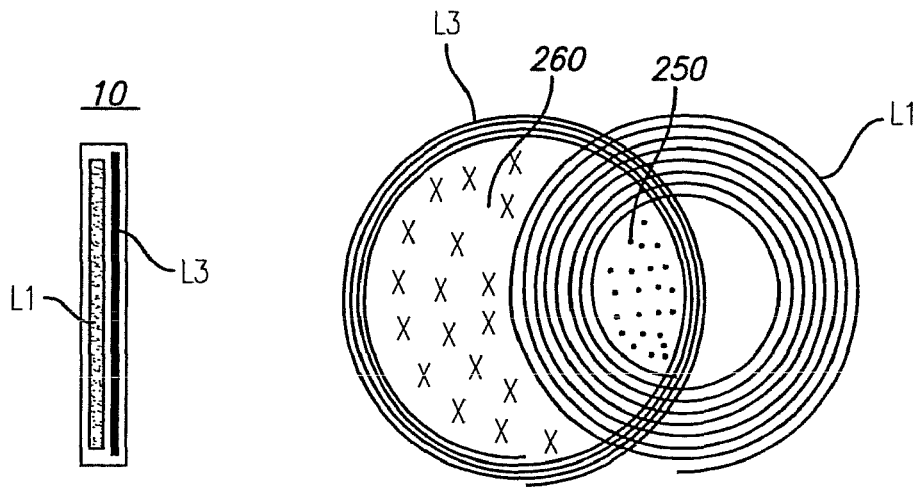
FIGS. 6A-6C show a third embodiment of the present disclosure.
Figure 6C:
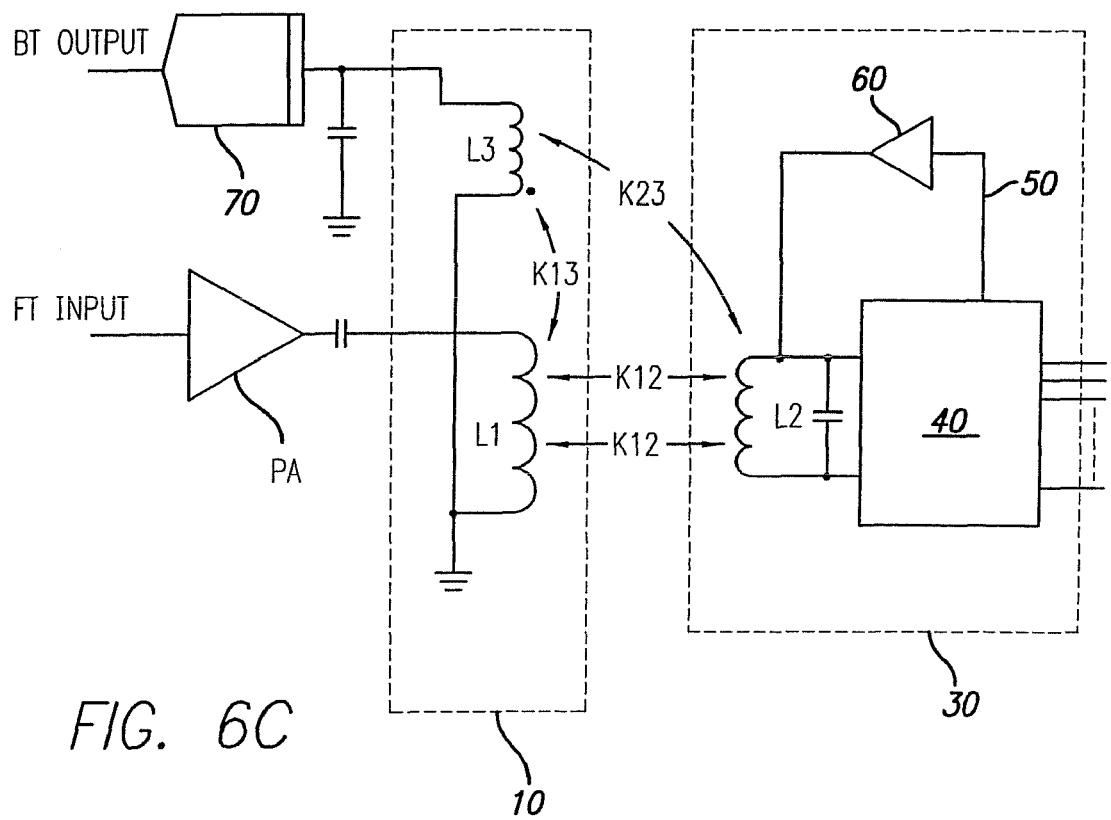

FIGS. 6A-6C show a further embodiment of the present disclosure, where the external coil assembly 10 is provided with one transmitting inductor L1 and one receiving inductor L3, as shown in FIG. 6A. The electrical behavior of the embodiment of FIG. 6A can be understood with reference to FIG. 6C, which is conceptually similar to FIG. 2. In the embodiment at issue, a single coupling coefficient is formed on the external coil assembly side, i.e. K13, which defines the coupling between L1 and L3. When the external coil assembly 10 interacts with implant coil L2, further coupling coefficients K12 and K23 are defined.

In accordance with this additional embodiment, K13 is made as proximate as possible to zero. This can be obtained, for example, by displacing L3 with respect to L1, when seen from the top, as shown in FIG. 6B. In particular, L1, when seen from the top or from the bottom, defines a bound internal (substantially circular in the embodiment of FIG. 6B) area and an unbound external area. Similarly, L3 also defines a bound internal area. The applicant has noted that K13 can be reduced to zero by displacing L3 with respect to L1 so that the internal area defined by L3 is spatially associated both with the internal area defined by L1 and the external area defined by L1. In particular, K13 can be reduced to zero when the magnetic flux B going through dotted area 250 has an intensity which is equal to the intensity of the magnetic flux B going through x'd area 260.

Figure 7A:
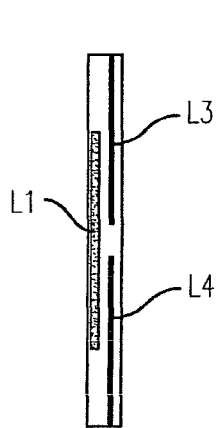
FIGS. 7A-7C show a fourth embodiment of the present disclosure, where the receiving coil has a differential configuration.
Figure 7B:
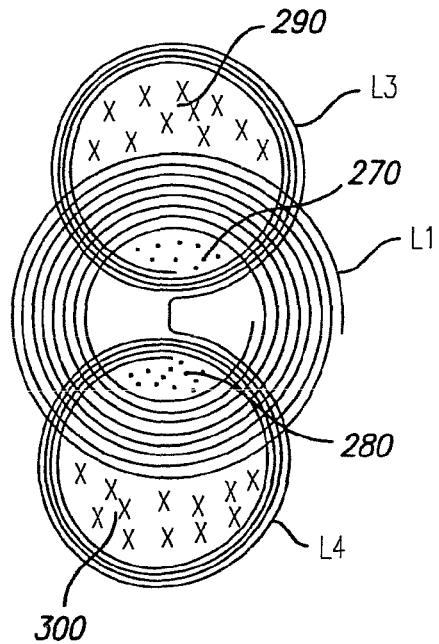
Figure 7C:
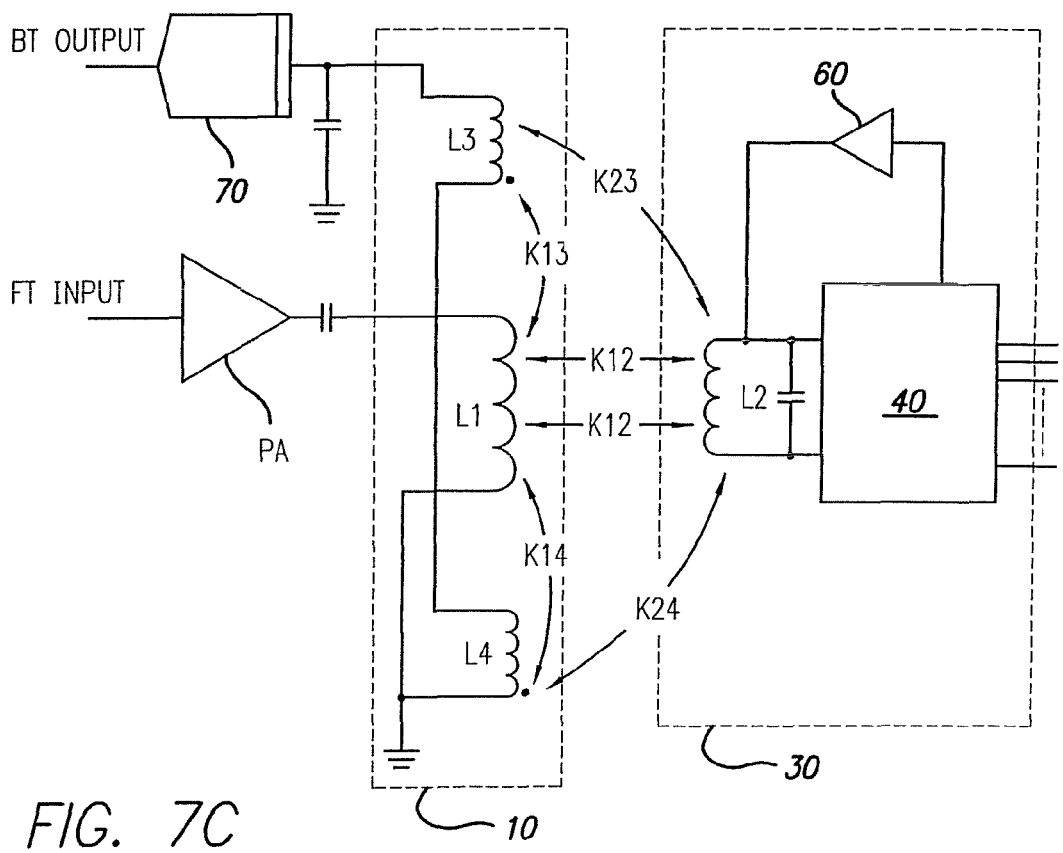

FIGS. 7A-7C show another embodiment of the present disclosure, where the external coil assembly 10 is provided with receiving inductors L3, L4 arranged on the same side of the transmitting inductor L1. The inductors L3, L4 can be seen as two distinct inductors or as a single inductor comprising portions L3, L4. The electrical behavior of the embodiment of FIG. 7A can be understood with reference to FIG. 7C, which is conceptually similar to FIGS. 4 and 6C. In the embodiment at issue, coupling coefficients K13 and K14 are formed on the external coil assembly side and coupling coefficients K12, K23 and K24 are formed when the external coil assembly 10 interacts with implant coil L2.

Given that both inductors L3 and L4 are located on the same side of inductor L1, the in-phase arrangement of L3 and L4 is different from that shown in FIG. 2, as shown by the position of the dots in FIG. 7C. Therefore, in this case, minimization of the combined coupling coefficient inside arrangement 10 is obtained by designing L3 and L4 so that K13=−K14. This can be obtained, for example, by displacing L3 and L4 with respect to L1, when seen from the top, as shown in FIG. 7B. Each of L3 and L4, when seen from the top or the bottom, defines an internal area. The applicant has noted that K13 can be made equal and opposite to K14 by displacing L3, L4 with respect to L1 so that the internal areas defined by each of L3 and L4 are spatially associated both with the internal area and the external area defined by L1. In particular, K13+K14 can be made equal to zero when the intensity of the magnetic flux B going through dotted areas 270, 280 is equal to the intensity of the magnetic flux B going through x'd areas 290 and 300.

Figure 8A:
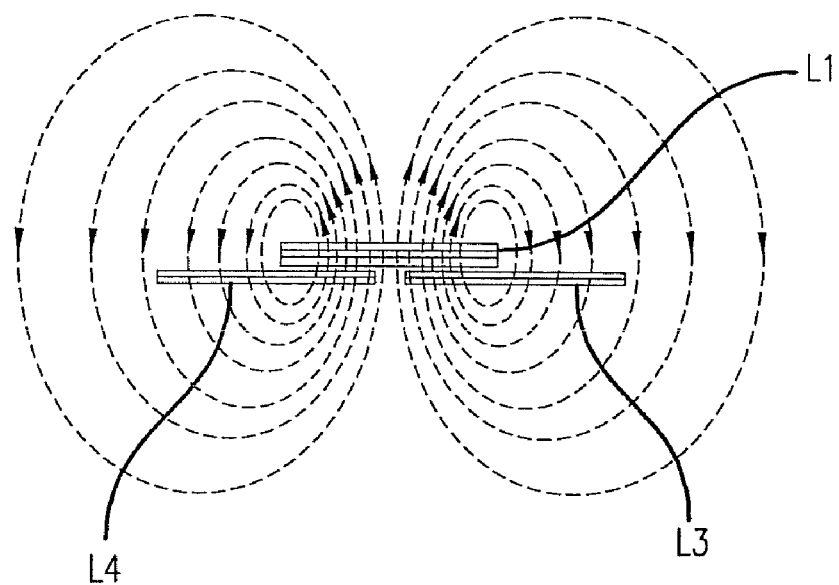
FIGS. 8A and 8B are magnetic flux diagrams helpful to understand the concept expressed with reference to FIG. 7B.
Figure 8B:
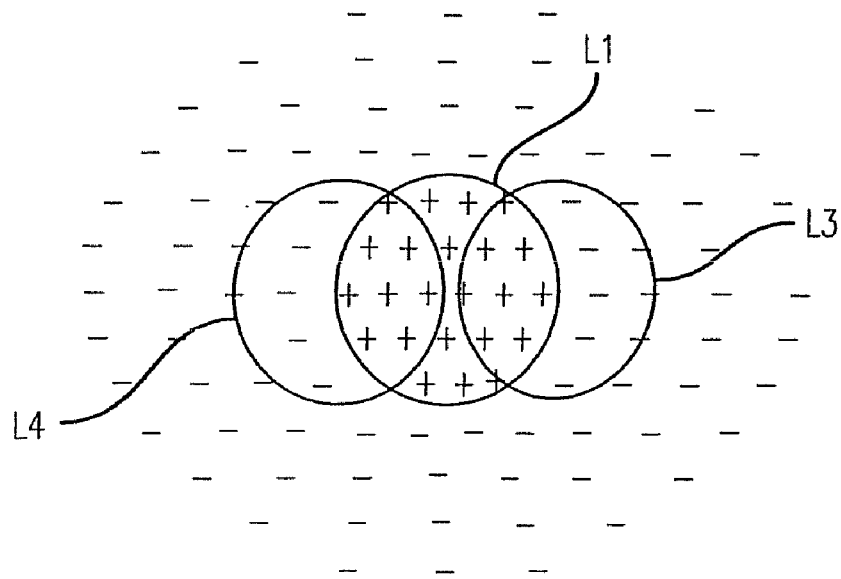

In other words, the magnetic field created by L1 is distributed in such a way that a) the direction of the field enclosed by the coil turns is opposite to the direction of the field surrounding them and b) the intensity of the field enclosed by the coil turns is equal to the intensity of the field surrounding the coil turns. A qualitative explanation of this concepts is shown in FIGS. 8A and 8B, where FIG. 8A shows a cross sectional view of the magnetic field distribution in the case at issue, and FIG. 8B shows a top view thereof. (+) field lines are outward field lines, while (−) field lines are inward field lines. The net magnetic fluxes passing through the receiving coils L3, L4 are minimized to zero, at which condition the effective coupling between the external transmitting coil L1 and the external receiving coils L3, L4 is negligent. In this way, the effect of the power carrier during reception is minimized while, at the same time, the forward coupling between the implant coil L2 and the external receiving coils L3, L4 still follows a size and distance relationship.

To maximize the receiving sensitivity, the receiving coil or coils should be tuned to the carrier frequency of the BT signal. The positioning of the receiving coil relative to the transmitting coil can be tuned by driving the transmitting coil with the transmitting coil with the power carrier frequency and monitoring the receiving signal strength of the same frequency at the receiving coil in the same time. The optimal position is where the signal strength is the lowest. In case of an inductively powered implant, the power carrier component received by the external receiver coil is composed of two parts: a part originating from the transmitting coil L1 and a part reflected from the implant coil L2 with a phase shift. Therefore, the position of the receiver coil L3 or L3, L4 should be tuned in the presence of the implant.

Figure 9:
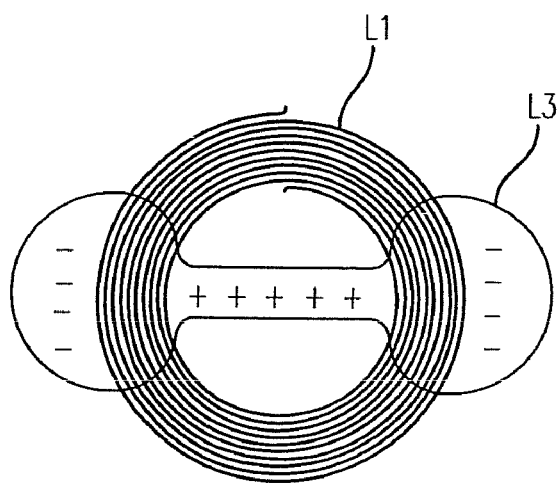
FIGS. 9-11 show alternative differential embodiments of the receiving coil of FIG. 7B.
Figure 10:
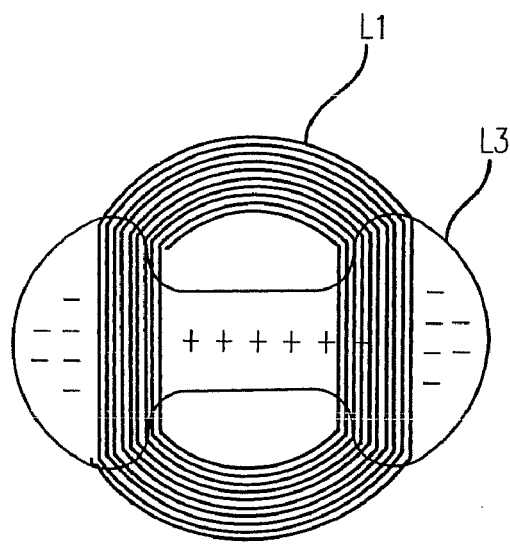
Figure 11:
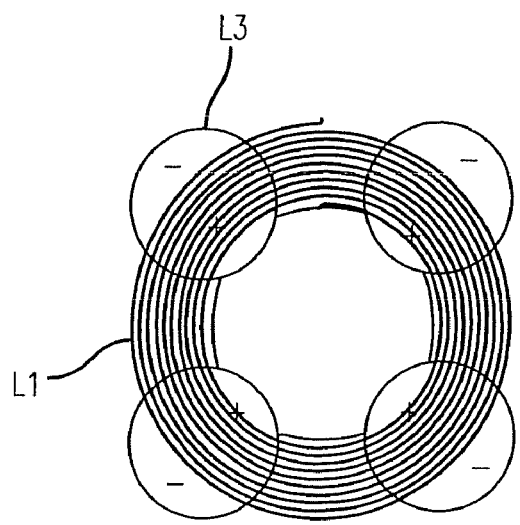

The embodiment shown in FIGS. 7A-7C is a differential embodiment. Similar embodiments are shown in FIGS. 9-11. The person skilled in the art will understand that those embodiments are for exemplary purposes only and that similar or different embodiments can be envisaged. In the embodiments of FIGS. 9-11, the windings of the wires of the receiving coil are not shown, for the sake of clarity. In the embodiment of FIG. 9, the receiving coil L3 is comprised of two substantially circular portions connected by an elongated portion. In FIG. 10, the receiving coil L3 is comprised of two substantially mushroom-shaped portions connected by an elongated portion. In FIG. 11, the receiving coil L3 is comprised of four substantially While several illustrative embodiments of the invention have been shown and described in the above description, numerous variations and alternative embodiments will occur to those skilled in the art. Such variations and alternative embodiments are contemplated, and can be made without departing from the scope of the invention as defined in the appended claims.

What is claimed is:

1. An inductive assembly adapted to be coupled with an implant on a human or animal body and to be located externally to the implant, the assembly comprising:

a first inductor, the first inductor defining a first area inside the first inductor and a second area outside the first inductor;

a second inductor located proximate to the first inductor, the second inductor having a symmetrical shape comprised of a first second inductor region and a second second inductor region, the first second inductor region defining a third area inside the first second inductor region, the second second inductor region defining a fourth area inside the second second inductor region, wherein intersection between the first area and the third area as seen from above the first inductor and the second inductor defines a first magnetic flux region passing through the first inductor and the second inductor, intersection between the first area and the fourth area as seen from above the first inductor and the second inductor defines a second magnetic flux region passing through the first inductor and the second inductor, intersection between the second area and the third area as seen from above the first inductor and the second inductor defines a third magnetic flux region passing through the first inductor and the second inductor, intersection between the second area and the fourth area as seen from above the first inductor and the second inductor defines a fourth magnetic flux region passing through the first inductor and the second inductor, and wherein, during operation of the inductive assembly, the first inductor is configured to create a magnetic field distributed in such a way that magnetic flux intensity through the first magnetic flux region is substantially equal and opposite to magnetic flux intensity through the third magnetic flux region and magnetic flux intensity through the second magnetic flux region is substantially equal and opposite to magnetic flux intensity through the fourth magnetic flux region.

2. The inductive assembly of claim 1, wherein the first second inductor region and the second second inductor region are circularly shaped.

3. The inductive assembly of claim 1, wherein the first second inductor region and the second second inductor region are mushroom shaped.

4. The inductive assembly of claim 1, wherein the second inductor further comprises a third second inductor region and a fourth second inductor region.

* * * * *